(12) United States Patent
Taylor

(10) Patent No.: US 6,666,099 B2
(45) Date of Patent: Dec. 23, 2003

(54) APPARATUS TO RECOVER SAMPLE GASES FROM FLUIDS

(75) Inventor: Brian Taylor, Calgary (CA)

(73) Assignee: Pason Systems Corp., Calgary (CA)

( * ) Notice: Subject to any disclaimer, the term of this patent is extended or adjusted under 35 U.S.C. 154(b) by 60 days.

(21) Appl. No.: 09/873,297

(22) Filed: Jun. 5, 2001

(65) Prior Publication Data

US 2002/0178842 A1 Dec. 5, 2002

(51) Int. Cl.⁷ .................................................. G01N 1/16
(52) U.S. Cl. .................................................. 73/863.12
(58) Field of Search ........................ 73/863.12, 863.02, 73/863.03, 54.35, 19.1, 19.12, 863.21, 54.31; 166/57

(56) References Cited

U.S. PATENT DOCUMENTS

| | | | |
|---|---|---|---|
| 3,222,135 A | * 12/1965 | Ashlmeed | 422/103 |
| 3,362,136 A | 1/1968 | Burnham, Sr. | |
| 3,831,352 A | 8/1974 | Parcels | |
| 3,856,483 A | 12/1974 | Rumpf et al. | |
| 3,895,927 A | 7/1975 | Bournhan, Sr. | |
| 3,973,930 A | 8/1976 | Burgess | |
| 4,251,483 A | * 2/1981 | Carrol | 422/50 |
| 4,272,258 A | 6/1981 | Shifflett | |
| 4,294,593 A | 10/1981 | Rehm | |
| 4,358,298 A | 11/1982 | Ratcliff | |
| 4,565,086 A | 1/1986 | Orr, Jr. | |
| 4,925,628 A | * 5/1990 | Metzger et al. | 422/100 |
| 5,181,419 A | 1/1993 | Thompson | |
| 5,199,509 A | 4/1993 | Wright et al. | |
| 5,367,546 A | * 11/1994 | Lau et al. | 367/392 |
| 5,648,603 A | 7/1997 | Hanson | |
| 6,047,239 A | * 4/2000 | Berger et al. | 702/9 |
| 6,157,893 A | * 12/2000 | Berger et al. | 702/9 |

FOREIGN PATENT DOCUMENTS

| | | | | |
|---|---|---|---|---|
| CA | 1208976 | * | 8/1986 | F04F/1/00 |
| EP | 259260 | * | 3/1988 | 251/214 |
| JP | 4-333795 | * | 11/1992 | 175/68 |

OTHER PUBLICATIONS

Derwent–ACC–No: 1979–K3754B Abstract of SU 646214 A, Feb. 8, 1979, Inventor: Belyi "Pneumatic Operation Representative Liquid Sampling Chamber—Uses Bellows-Operated Separator and Diaphragm Permitting Extraction of Undisturbed Flow Sample".*

* cited by examiner

*Primary Examiner*—Thomas P. Noland
(74) *Attorney, Agent, or Firm*—Blake, Cassels & Graydon LLP; Terry L. Leier

(57) ABSTRACT

A gas sample extraction apparatus to recover sample gases from fluids such as the return flow drilling mud of an oil and gas well has a sample canister forming a sample chamber with a fluid inlet port and a fluid outlet port. The gas sample extraction apparatus is disposed in a flow of fluid to be sampled, and the fluid sample flows through the sample chamber via the fluid inlet and outlet ports. A bubbler enclosure is in fixed relationship to the sample canister and has an exit bubbler port at the desired fluid level of the sample chamber. Compressed air is supplied to the gas sample extraction apparatus to maintain the fluid sample level within the sample canister at the desired fluid level.

18 Claims, 6 Drawing Sheets

APPARATUS TO RECOVER SAMPLE GASES FROM FLUIDS

FIELD OF THE INVENTION

This invention relates to a system for the collection and extraction of gases entrained in a fluid, and more particularly, hydrocarbon gases in the return flow drilling mud material of an oil or gas exploration well.

BACKGROUND OF THE INVENTION

There is a demand for apparatus to collect gases emitted from and extract gases entrained in fluid and slurry materials. For example, gases entrained in the return flow material discharged from an oil or gas exploration well. This return flow material is generally in the form of a mud stream and is usually referred to as drilling mud. Collection, extraction and analysis of drilling mud gases can be used to indicate the hydrocarbon content in the well return flow material which, in turn, provides the basis for an assessment of the formation and any indications that the well drilling has hit a producing zone. In an oil and gas well, generally the primary hydrocarbon gas of interest is methane gas. Thus, information relating to the methane gas content of the well return flow material is the information that is usually of most interest. Although, under certain drilling conditions, there is also interest in information relating to some of the other hydrocarbons that may be present in the well return flow material.

The gases obtained from the return flow material discharged from the oil or gas exploration well are sampled for analysis. A gas collection, extraction device provided for this purpose is generally referred to as a gas trap. The gas trap apparatus is typically positioned in a "Shaker Box" or "Possum Belly" of a "Shaker Tank" into which the well return material is directed when it exits the well bore. Generally, the gas trap provides the collected, extracted gases to a sample tube extending from the gas trap to the sample analysis equipment. The sample tube typically has a small diameter and the collected gas sample is transported in the sample tube to sample analysis equipment on a continuous basis.

The current state of the art drilling mud gas sample collection, extraction systems have several problems that cause such systems to require high maintenance costs and attention. Current gas trap apparatus provides a canister with an electric motor mounted on top, which drives a centrifugal impeller housed centrally within the canister. The canister has a plate on the bottom with a small hole in the centre that acts as an inlet for the drilling mud. Another hole is provided in the side of the canister that forms an outlet for the drilling mud to be expelled from. This arrangement is designed both to pump mud through the gas trap sample canister and to agitate the mud contained within the sample canister sufficiently to permit entrained gases to be released. The gases are released from the return drilling fluid well mud stream as gas bubbles and are evacuated from the sample canister via a sample outlet, which couples to a sample tube.

Current gas traps are quite heavy, usually weighing 70 lbs. or more making the devices relatively heavy and, consequently, onerous to install, operate and maintain. Generally, the gas traps are attached to the shaker box and disposed inside of the shaker box, positioned at a particular depth in the drilling mud flowing through the shaker box. Typically, the apparatus for attaching the gas trap to the shaker box includes a bracket that permits up and down adjustment of the gas trap to allow the gas trap to be positioned at the correct depth in the drilling fluid. Positioning the gas trap at the prescribed or optimum depth in the drilling fluid is very important with the current design of gas traps. Any variation from the optimum depth causes the gas trap to change the amount of drilling mud it will pass in a given period of time as well as causing it to liberate more or less entrained gases from the drilling mud in that same given period of time. Furthermore, if the level of the drilling mud rises too high, drilling mud will be drawn into and through the sample tube by the sample pump toward the sample analyzer causing contamination of the equipment. Depending on the amount of drilling mud drawn into the sample tube, the sample handling, conditioning and analysis systems can all become contaminated with the drilling mud. At a minimum, drawing drilling mud into the sample tube will cause contamination that will require maintenance intervention and may necessitate replacement of the sample tube. In operation, most shaker boxes will experience a change in drilling mud level as the mass flow quantity of drilling mud changes or as the density and viscosity of the drilling mud changes. Drilling mud level changes in the shaker box can also occur as a result of the rig crew making adjustments to the shaker box itself.

Current oil and gas well drilling gas traps require operational maintenance and attention to operate in harsh winter environments. For example, the collected gas sample is typically delivered to analysis equipment that often is distances of hundreds of feet from the gas trap. A sample tube effects delivery of the sample, which is subject to freezing in the winter. Consequently, the sample is dehumidified to avoid freeze-up in the sample tube. Dehumidification apparatus typically includes a glycol dryer that the sample is bubbled through. The moisture removed from the sample causes the vessel holding the glycol to become full, requiring replacement of the glycol to rejuvenate the apparatus. Another, dryer apparatus generally found is a solid desiccant, for example calcium chloride, to further dry the sample. The solid desiccant will require replacement, often several times per day, to maintain operation of the dehumidifier systems. An example of such type of systems is described in U.S. Pat. No. 4,565,086 to Orr.

U.S. Pat. No. 5,199,509 to Wright for a controlled gas trap system provides a gas trap forming a sample chamber having an inlet and outlet both submersed in the fluid to be sampled. Disposed within the gas trap is a rotating agitator and a vent to admit substantially gas-free air into the housing and a means to draw off the gas evolved from the mud. To provide for varying mud levels, the apparatus of Wright relies on the rotation of agitator to maintain a constant mud level within the sample chamber.

U.S. Pat. No. 5,648,603 to Hansen describes a method and apparatus for stabilizing a quantitative measurement gas trap used in a drilling operation. The method involves providing a known quantity of standard gas for injection to the trap in which the gas stream is evolved, for example Ethylene, Isobutylene and Nitrous Oxide.

It is desirable to have a drilling mud gas sample collection, extraction system that is operable over a range of drilling mud levels within the sampled flow stream, for example, in a shaker box.

It is desirable to have a drilling mud gas sample collection, extraction system that operates consistently over a wide range of ambient temperatures, including freezing winter temperatures.

It is desirable to have a drilling mud gas sample collection, extraction system that operates consistently over a wide range of drilling mud viscosity.

It is desirable to have a drilling mud gas sample collection, extraction system that operates with little or no frequent operator maintenance or intervention.

SUMMARY OF THE INVENTION

The invention provides a gas trap assembly to recover sample gases from fluids having pneumatic motor driven agitator blade rotatably disposed within a gas sample collection canister. To enable operation of the pneumatic motor in winter conditions, the pneumatic motor compressed air supply has an air dryer to dry the air supply to a dew point below minus 40 degrees Celsius. The compressed air treatment system is housed in a heated environment to prevent the water extracted from the air from freezing up.

For operation in winter environments, a heater heats the motor compressed air supply. The heated compressed air is delivered to the gas trap to power the gas trap pneumatic motor. Before going to the motor at the gas trap, the heated compressed air is passed through a heat exchanger on the gas trap to warm the gas trap apparatus to ensure the sample gas is maintained at a temperature above its dew point and prevent freezing. Sample gas recovered from the fluid is supplied to a sample tube for transport to analysis equipment. In the preferred embodiment, the sample tube is bundled together with the air supply tube inside an insulated jacket. This arrangement transfers heat from the heated compressed air supply tube to the sample tube to keep the sample gas warm until it arrives at the analyzer equipment.

Within the gas trap, changing mud levels in the fluid flow in which the gas trap is disposed are controlled to a set or predetermined level using compressed air. To maintain the drilling fluid mud level at a consistent level within the gas trap, a two-chamber configuration is employed comprising a sample canister forming the first chamber and a bubbler enclosure or canister forming a second chamber. Compressed air is supplied in common to both chambers, consequently, the bubbler enclosure regulates the pressure within the sample canister to keep the mud level within it constant. The bubbler enclosure is sealed at the top and has an air exit port opening at the bottom at the level or point where the mud level in the sample canister is desired to be. The exit port opening at the bottom of the bubbler enclosure may be provided by cutting off the bubbler enclosure at the desired length. In operation of the gas trap, pressurized air is supplied to bubbler enclosure. The chamber formed by the bubbler enclosure is in common air communication with the sample chamber of sample canister through a passageway equalizing the pressure in the two chambers.

To operate the gas trap, the amount of air supplied to the bubbler enclosure is slightly greater than the amount of sample gas drawn from the chamber formed by the sample canister. Therefore, the bubbler enclosure will always be bubbling air out of the bottom as long as it is under the surface of the mud. The cavities formed by the bubbler enclosure and the sample canister are in communication with each other, consequently, the mud level maintained by the air pressure within the bubbler enclosure causes the mud level inside the sample canister to be at the same level. Variations in the drilling mud level exterior to the gas trap in the shaker box can rise a great deal without having any effect on the level of the drilling mud within the sample chamber of the gas trap. With this arrangement, the gas trap is prevented from "flooding", that is, the condition where drilling mud is sucked up into the sample tube. In the event that main air pressure is lost, it would be possible for the gas sample extraction pump to suck the drilling mud into the sample tube following main air pressure loss.

In a preferred embodiment, the sample canister provides baffles projecting into the sample cavity formed by the sample canister. The baffles prevent or reduce mud fluids from entering into the sample tube.

To prevent or reduce contamination of the sample tube and to remove condensed moisture that may be collected in the sample tube, the sample tube can be purged when the flow of sample gas through the sample tube falls below a lower threshold. To purge the sample tube, pressurized air is supplied to the sample tube causing a gas flow through the sample tube that is the reverse of the sample gas flow. Preferably, the reverse flow pressurized air is supplied at higher flow rates and pressures than that of the sample gas.

In one of its aspects, the invention provides an apparatus to recover gases from a fluid that includes a sample canister submersible in a fluid. The sample canister forms a sample cavity and has a fluid ingress port and a fluid egress port to provide a path for the flow of fluid through the sample cavity of the canister. A sample extraction port is exterior to the sample canister and in communication with the sample cavity. A bubbler enclosure is attached to the sample canister and has an exit port at a predetermined location in relation to the sample container and a supply port adapted to receive a supply of pressurized gas. A passage extends between the sample canister and the bubbler enclosure to provide a path for communication of pressurized gas from the supply port to the sample cavity of the sample canister. When the sample canister is submersed in a fluid, a supply of pressurized gas to the inlet port of the bubbler enclosure will result in a level of fluid within the sample cavity of the sample canister that is correspondingly set by the exit port location of the bubbler enclosure.

In another of its aspects, the invention provides an apparatus to recover gases from a fluid that has a sample container adapted for submersion in a fluid. The sample container forms sample cavity therein and includes a fluid ingress port and a fluid egress port to provide a path for the flow of fluid through the sample cavity of the container. A sample extraction port is exterior to the sample container and in communication with the sample cavity. Agitator means is rotatably disposed within the sample cavity of the sample canister and a motor drives the agitator. A bubbler enclosure is attached to the sample container and has an exit port at a predetermined location in relation to the sample container. A supply port is adapted to receive a supply of pressurized gas into the bubbler enclosure and a passage extends between the bubbler enclosure and sample container to provide a path for communication of pressurized gas from the supply port to the sample cavity of the sample container.

In yet another of its aspects, the invention provides apparatus to recover gases from a fluid operable in freezing conditions including a sample container adapted for submersion in a fluid. The sample container forms a sample cavity therein and a fluid ingress port and a fluid egress port to provide a path for the flow of fluid through the sample cavity. A sample extraction port is exterior to the sample container and in communication with the sample cavity. An agitator is rotatably disposed within the sample cavity of the sample canister and motor means is provided to drive the agitator. A bubbler enclosure is attached to the sample container and has an exit port at a predetermined location in relation to the sample container. A supply port is adapted to receive a supply of pressurized gas and a passage extending between the sample container and the bubbler enclosure provides a path for communication of pressurized gas from the supply port to the sample cavity and the bubbler enclosure. The apparatus also includes a source of pressurized air and a heater to heat the pressurized air. A heat exchanger block is disposed on a frame supporting the sample canister and the bubbler enclosure to recover heat from the pressurized air.

And in yet another of its aspects, the invention provides apparatus operable in freezing conditions to warm a gas recovered from a well drilling return flow fluid. A sample tube receives a gas recovered from a well drilling return flow fluid and a second tube is adapted to receive a source of heated air that axially coextends with said sample tube to facilitate heat exchange between them.

In another aspect, the invention provides apparatus to facilitate transport in freezing conditions of a sample gas recovered from a fluid that includes at least two longitudinal co-extending hoses forming a common surface there along. The hoses are adapted to facilitate heat exchange between them. One hose is for transport of a sample gas and the other hose is for transport of heated air. A sheath surrounds the co-extending hoses providing the capability to transfer heat energy is from the heated air hose to the sample gas hose.

In yet another of its aspects, the invention provides apparatus to indicate the relative viscosity of a fluid including an agitator adapted for rotatable placement in a viscose fluid. A pneumatic motor is provided to effect rotation of the agitator. A variable valve controls the supply of compressed air to the pneumatic motor means in response to a control signal produced by a controller. A sensor produces rotation signalling representative of the rotation of the agitator for the controller. The controller operates to maintain a substantially constant rate of rotation of said agitator by varying the control signal with relative changes in fluid viscosity.

In another of its aspects, the invention provides a self cleaning apparatus to recover gases from a fluid including a sample container submersible in a fluid. The sample container forms a sample cavity and has a fluid ingress port and a fluid egress port to provide a path for the flow of fluid through the sample cavity of the sample container. A sample extraction port is exterior to the sample container and in communication with said sample cavity. A means to draw a flow of gas through the sample extraction port causes a flow of gas through the sample extraction port in a supply direction. The invention has a flow valve operable to connect a source of compressed air to the sample extraction port to effect a flow of compressed air through the sample extraction port in a direction reversed to the supply direction. Activation means effects operation of the flow valve. The activation means operates the flow valve when the flow of gas through the sample extraction port is too low or periodically.

The preferred embodiments of the invention will now be described with reference to the attached drawings, which are briefly described as follows:

DETAILED DESCRIPTION OF THE PREFERRED EMBODIMENT

Figures 1, 2:
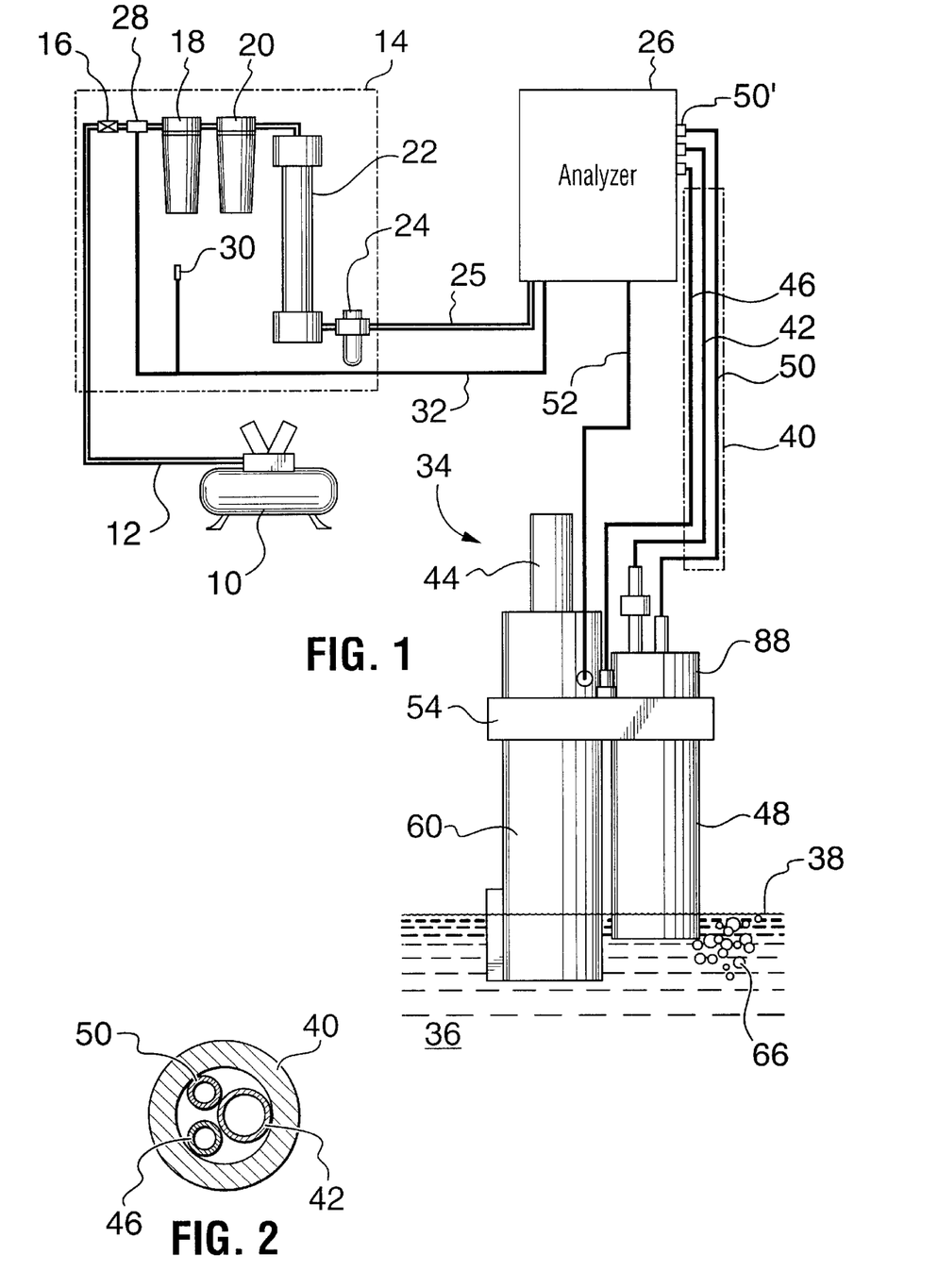
FIG. 1 shows a functional block diagram of a preferred embodiment of a sample gas extraction apparatus in accordance with the invention and a supply air system.
FIG. 2 is a cross-section view of the air tubes of FIG. 1.

In the drawings and this detailed description, the same reference numbers are used to denote like features of the invention throughout the various figures. Reference is made to FIG. 1, which shows a functional block diagram of a preferred embodiment of the sample gas extraction apparatus and a compressed air supply system. A rig compressor 10 provides a source of compressed air, which is supplied via compressed air supply hose or tube 12 to a heated enclosure housing 14, shown in dotted outline form, that contains equipment to extract moisture from the air supplied in compressed air supply tube 12. Heated enclosure housing 14 is provided to prevent water extracted from the compressed air from freezing when the system is in operation in winter conditions. A valve 16 controls the ingress of air to the dryer equipment. A separate filter 18 is provided to remove particulate matter or oils from the compressed air. A coalescing filter 20 provides a first dryer apparatus to remove moisture from the air. A membrane dryer 22 is provided to further remove humidity from the air and is capable of reducing humidity in the air to a dewpoint of −40° C. A regulator 24 controls the pressure of the air leaving the heated enclosure 14. The dried air is supplied to analyzer apparatus 26, generally shown by box 26. A pressure sensor 28 provides an indication of the pressure of the air supplied from rig compressor 10. A temperature sensor 30 is provided to measure the temperature within heated enclosure housing 14. The pressure and temperature signalling are supplied to analyzer 26 on a dryer signalling line 32.

Apparatus to recover gases from a fluid, or gas trap, constructed in accordance with the invention, generally depicted by reference numeral 34, is positioned within a fluid 36, for example, a well drilling mud return flow. The gas trap 34 is positioned in the fluid so as to place the lower portion of the gas trap below the surface level of the fluid mud level 38 to facilitate extraction of a gas sample by the gas trap from the fluid well return flow 36. The gas trap 34 is connected to analyzer equipment 26 by an insulated sheath 40, which houses air supply tubes running between the analyzer 26 and gas trap 34. A primary air supply tube 42 is used to supply air to drive the pneumatic motor 44 of the gas trap. A bubbler air supply tube 46 supplies air to a bubbler enclosure 48 of the gas trap 34. The sample gas recovered by the gas trap 34 from the fluid 36 is collected within the gas trap 34 for transport to the analyzer 26 via sample supply tube 50. Preferably, transducers monitor the operation of gas trap 34 provided in the gas trap to measure the gas trap temperature and the gas trap pneumatic motor 44 rpm. Signalling from these transducers is supplied to analyzer 26 by trap signalling line 52.

FIG. 2 is a cross-section view of the air hoses or tubes of FIG. 1. The primary air supply hose or tube 42 is disposed within sheath 40 along with the bubbler tube 46 and the sample tube 50. The three hoses are disposed inside sheath 40, which provides protection for the tubing and is preferably insulated to reduce heat loss to the exterior of sheath 40. The tubes 42, 46 and 50 are preferably in contact with each other to facilitate heat exchange therebetween.

Figure 3:
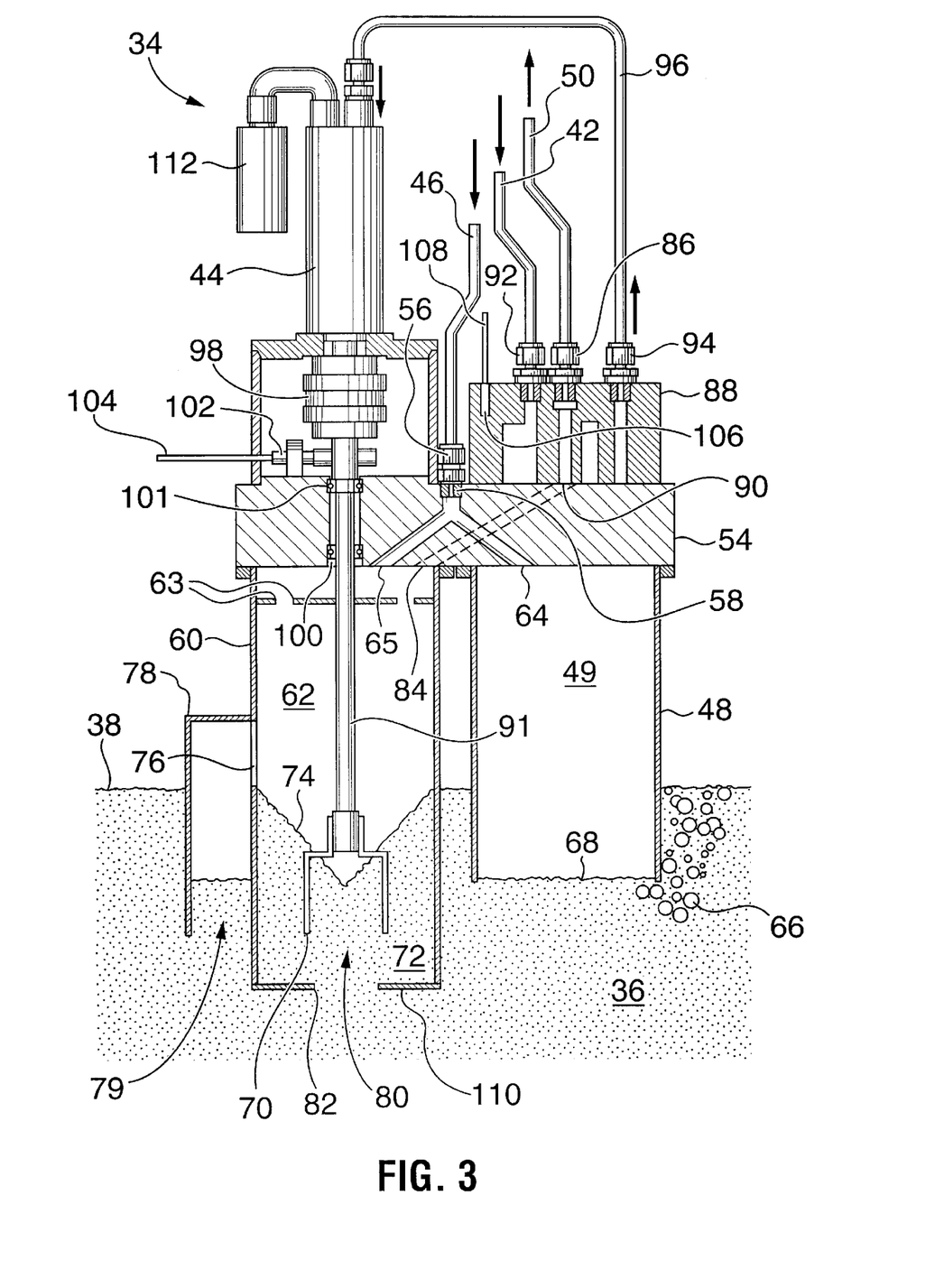
FIG. 3 is a partial cross-section al view of the gas trap of FIG. 1.

FIG. 3 shows a partial cross-sectional view of the gas trap 34 of FIG. 1. The gas trap has a main frame 54 to provide a mounting structure for the components of the gas trap. A bubbler enclosure 48 extends downwardly from frame 54. Bubbler enclosure 48 forms a cavity to receive the bubbler air supplied by bubbler supply tube which couples to a fitting 56, which supplies the bubbler air to the bubbler enclosure 48 via a bubbler air passage 58 in main frame 54. The bubbler air passage 58 can be drilled through main frame 54. Fitting 56 includes a conventional coupling nipple that can be mounted on frame 54, for example, by threading engagement with main frame 54, to provide a mount for the sleeve coupling of the bubbler tube 46 to mate with. A common passage 64 extends through frame 54 to openings provided in bubbler cavity 49 and sample cavity 62. In this embodiment, only one opening of common passage 64 is required in the bubbler cavity 49, which is for the common passage 64 and also serves as the supply port for bubbler air received at the gas trap via the bubbler air supply tube 46.

The gas recovered from the fluid 36 is collected in a sample canister 60, which extends down from frame 54 to form an interior sample collection cavity 62. The sample collection cavity 62 is in communication with the cavity 49 formed by the bubbler enclosure 48 via passage 64 extending therebetween. To use the gas trap, the lower portion of the gas trap is submersed within a fluid 36. A supply of compressed air is provided to the gas trap via the bubbler air supply tube 46. The compressed air is contained within the bubbler enclosure 48 that becomes pressurized with the compressed air supplied to cavity 49. When cavity 49 fills with compressed air, bubbles 66 escape from the lower extremity of bubbler enclosure 48 into the fluid 36 that the gas trap has been positioned in, for example, well drilling mud return flow. The compressed air causing pressurization of the cavity 49 of the bubbler enclosure 48 is applied also to the sample collection cavity 62 of the sample canister 60 as the cavities 49 and 62 are in communication via passage 64. The common pressurization of cavities 49 and 62 causes the fluid level within cavity 62 of the sample tube to be at the same level as the fluid within cavity 49 of the bubbler enclosure 48.

The bubbles 66 will not exit the bubbler enclosure 48 until the cavity mud level 68 reaches a level where the compressed air supply can exit the cavity 49 of the bubbler enclosure 48. The preferred manner of controlling the bubbler cavity compressed air exit level, and therefore the fluid level in the bubbler cavity 49, is simply to cut the bubbler enclosure 48 at the desired length. This manner of construction leaves a relatively large exit opening from bubbler enclosure 48 which avoids fouling and plugging of the exit opening by the mud 36. The lower extremity of bubbler enclosure 48 is positioned or disposed relation to the sample canister 60 to select or locate the desired fluid mud level within sample canister 60.

The quantity of compressed air supplied to bubbler enclosure 48 via the bubbler air supply tube 46 is set, for example at the analyzer 26, to supply a quantity of air that is slightly more than the gas sample which is extracted from sample cavity 62. In this manner, the excess air supplied to cavities 49 and 62 will be sufficient to cause bubbles 66 to exit bubbler enclosure 48 at the exit opening, for example, at the foot thereof. Consequently, irrespective of the mud level 38 exterior to the gas trap, the cavity mud level 68 will always be located at the foot of the bubbler enclosure 48. Because bubbler cavity 49 is in communication with sample cavity 62 via passage 64, the average mud level within cavity 62 will be at the same level as the cavity mud level 68.

In the interior of sample canister 60 is an agitator 70 that is driven in rotation by pneumatic motor 44. In operation, agitator 70 will rotate at an angular velocity of approximately 1700 rpm. The rotation of agitator 70 within the fluid 72, for example well drilling mud, contained within the sample canister 60 will cause the well drilling mud to be agitated or whipped and to develop an inclined conical surface 74.

Sample canister 60 has an egress port 76 formed in the lower portion thereof at a position such that the upper portion of conical surface 74 will extend toward egress port 76. While agitator 70 is rotating, a continuing portion of the well drilling mud agitated by agitator 70 will reach upward toward egress port 76 where it will overflow into egress port 76 to exit sample canister 60 for return to the well drilling mud main fluid flow 36. To prevent exchange of gases between the interior and exterior of sample canister 60 through egress port 76, a baffle 78 is provided. Baffle 78 forms an opening 79 that is below both the surface 38 of the well drilling mud fluid 36 and below the mud level 68 of the cavity in the bubbler enclosure 48. The opening 79 is below the mud level 68 in the bubbler enclosure 48 to ensure that the excess compressed bubbler air exits only out of the bubbler cavity via bubbles 66 and does not flow through the sample cavity 62. Replenishment fluid, for example drilling mud, enters the chamber or sample cavity 62 of the sample canister 60 in the direction of arrow 80 through ingress port 82. Naturally, ingress port 82 is below the fluid level 68 set by the bubbler enclosure 48. Agitation of the sampled well drilling mud fluid 72 within sample canister 60 by agitator 70 assists to release gases into sample cavity 62 that are entrained in the well drilling mud mixture.

Collected sample gases are evacuated or extracted from sample cavity 62 via port 84. The gas sample extraction port 84 is in communication with sample outlet coupling 86 to permit coupling of a sample transport tubing to the gas trap to permit the extracted gas sample to be transported to analysis equipment. To prevent contamination of the sample gas pathways, baffles 63 extend from the sample canister wall and agitator shaft 91 and act to block splashing mud from reaching and fouling the sample port 84.

Figure 5:
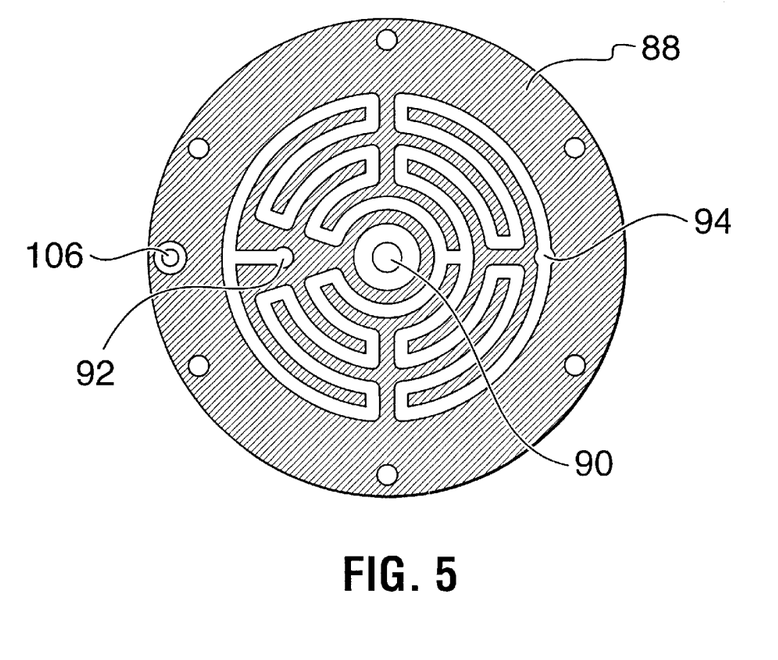
FIG. 5 is a top cross-sectional view of the heat exchanger of FIG. 1.

Because the extracted gas sample is recovered from a fluid flow, the recovered gas sample will be high in humidity. To prevent the humid sample gas from freezing in transport to the analysis equipment during winter conditions, it is preferable to heat the gas sample. In the preferred embodiment, the gas trap apparatus and gas sample is heated by a heat exchanger block 88. The heat exchanger block 88 imparts heat to the gas trap apparatus, in particular to frame 54 on which it is mounted, from the heated air supply provided to the gas trap to operate pneumatic motor 44. Any suitable heat exchanger may be used, for example, a maze heat exchanger as shown in cross section in FIG. 5. The heat exchanger has a sample inlet 90, in FIG. 5, that is in communication with the sample outlet coupling 86. A sample inlet 90 provides the source of sample gas to the heat exchanger block 88. The primary air supply tube 42 is coupled to supply coupling 92 to provide a supply of heated air to heat the gas trap and to heat the sample gases that are passing through the heat exchanger, when ambient temperatures warrant heating. The supplied air then exits the heat exchanger block 88 at main air supply exit 94 where it is transported to the pneumatic motor 44 by motor supply tube 96.

Pneumatic motor 44 is coupled to agitator 70 via a coupling 98. A seal 100 is provided on the cavity side of frame 54 to keep debris and moisture from escaping the sample cavity 62 and fouling the bearings 101 disposed between agitator shaft 91 and frame 54. A rotational sensor 102 is provided to produce signalling representative of the revolutions per minute (rpm) of agitator shaft 91. The RPM signalling is output on line 104 for use by monitoring equipment, for example, by analyzer 26. The temperature of the sample gas leaving the gas trap is measured by a gas trap sample temperature sensor 106, which provides sample temperature signalling on line 108 for use by monitoring equipment, for example, by analyzer 26.

Figure 4:
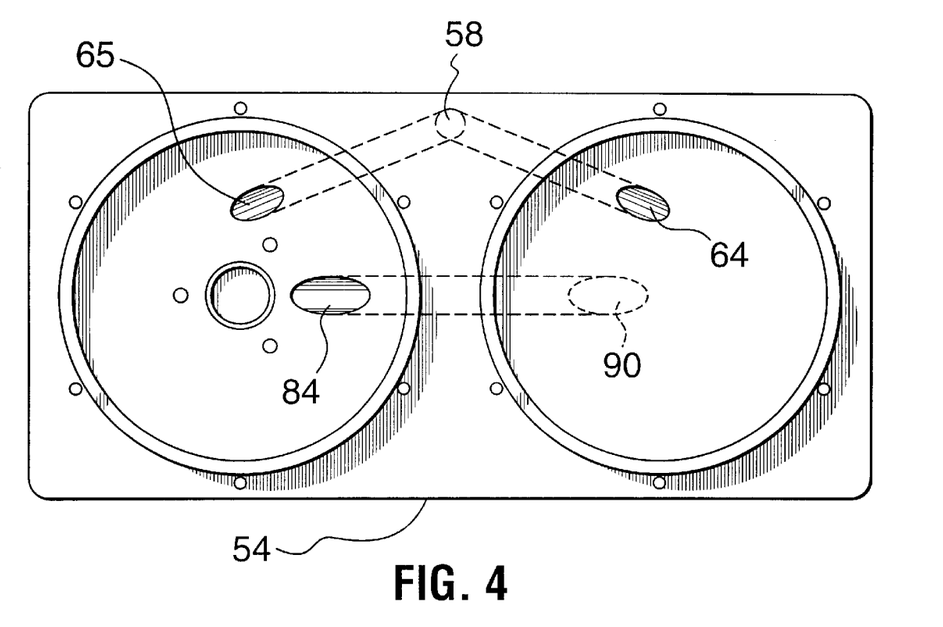
FIG. 4 is a bottom plan view of the gas trap frame of FIG. 1.

FIG. 4 is a bottom plan view of the frame of FIG. 1. For clarity, the frame 54 is shown without the other apparatus of the gas trap attached. The left portion of the frame forms the upper side of the sample chamber side. The gas sample extraction port 84 is in communication with the heat exchanger gas inlet 90. Gas inlet 90 is on the reverse side of the frame 54 and, therefore, is shown in hidden dotted outline form in the drawing. An opening 65 for passage 64 is shown disposed within the sample chamber. The right side of the frame forms the upper side of the bubbler chamber shown with the opening for passage 64 depicted.

Figure 6:
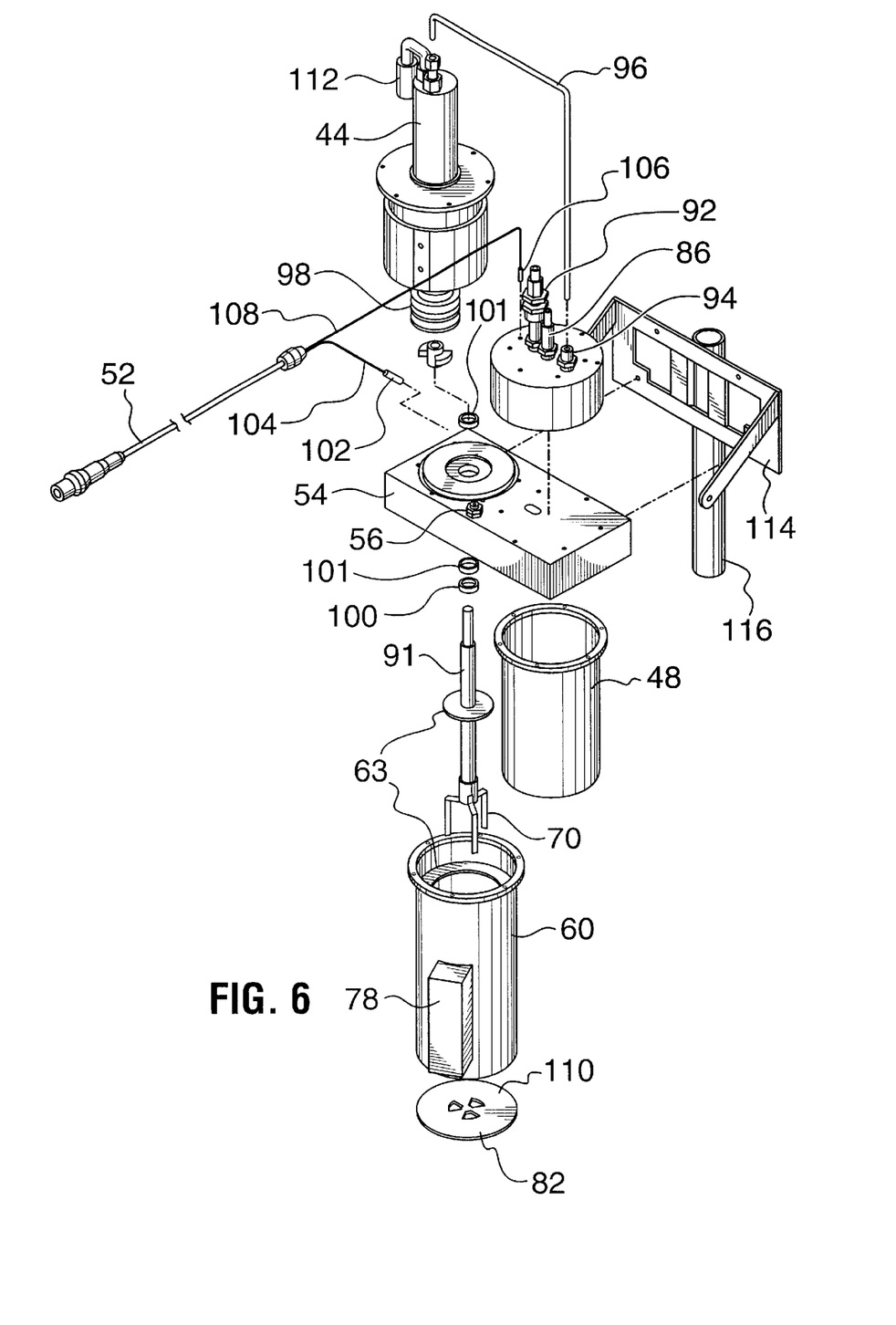
FIG. 6 is an exploded schematic view of the gas trap of FIG. 1.

FIG. 6 is an exploded schematic view of the gas trap apparatus of FIG. 1. The sample canister 60 has a removable bottom 110, which forms the fluid ingress port 82 for the sample canister. A coupling 98 couples motor 44 to the agitator shaft 91. An exhaust muffler 112 is provided for exhaust air discharged from pneumatic motor 44. A mounting bracket 114 is attachable to a main frame 54 and includes arm 116 which couples to a mounting bracket on the shaker box to which the gas trap will be mounted. The trap signalling line 52 contains the sensor signalling lines 104 and 108 therein.

Figure 7:
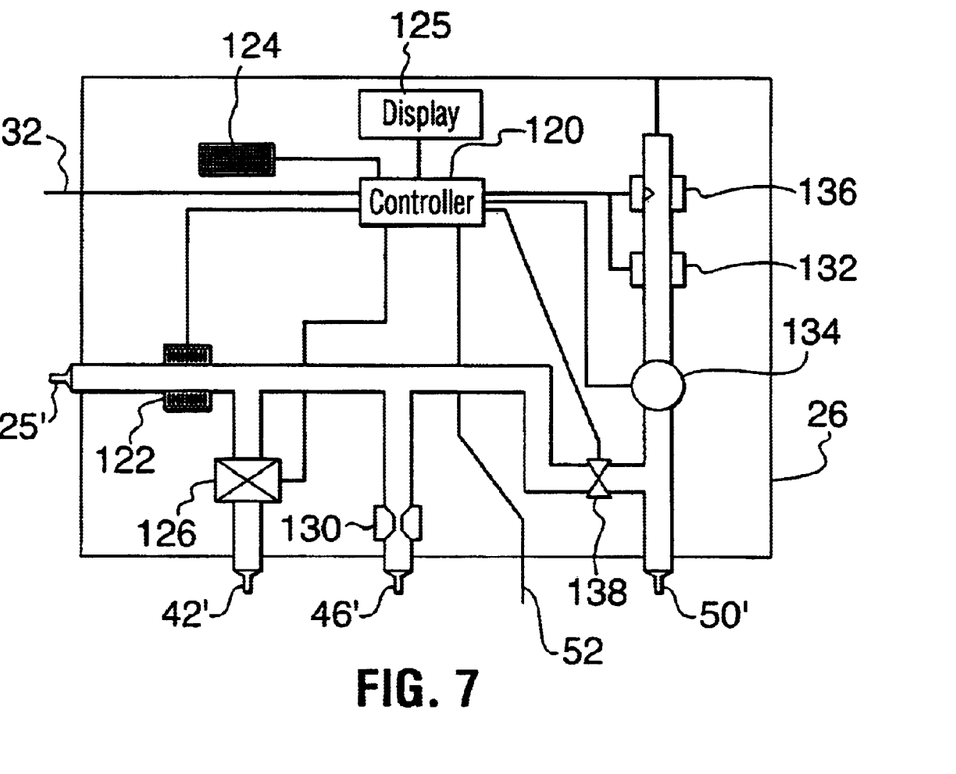
FIG. 7 is a functional block diagram of a controller apparatus to operate the sample gas extraction apparatus.

FIG. 7 is a functional block diagram of an embodiment of controller apparatus to operate of the sample gas extraction apparatus of FIG. 1. Analyser 26 has a controller 120 which is a computer that receives signalling from the elements of the sample gas extraction apparatus and produce control signalling. The controller 120 controls the operation of the analyser and gas trap apparatus in the manner described in more detail hereafter.

The pressure and temperature signalling from the sensors 28 and 30 located in the heated enclosure 14 is supplied to the analyser 26 on the dryer signalling line 32. The compressed air is supplied to the analyser via supply hose 25, which is coupled to the analyzer at fitting 25'.

The gas trap 34 has a trap signalling line 52, two air tubes 42 and 46, and a sample tube 50 running between it and the analyser 26. The trap signalling line 52 connects two sensors to the analyser, that is, a proximity or rotational sensor 102 which measures the RPM of the pneumatic motor 44 and a temperature sensor 106 to measure the temperature at a suitable location of the gas trap, for example, the heat exchanger block 88. The analyser controller 120 controls both the motor RPM and the temperature of the gas trap as described in more detail subsequently. The tubes are in contact along their length in the run from the analyser 26 to the gas trap 36 to provide a counter flow heat exchange to facilitate heat flow between the air tubes 42, 46 and the sample tube 50. The tubes are surrounded by insulated sheath 40 which impedes heat loss through sheath 40.

The compressed air supplied to the gas trap 34 from the analyser 26 in the main air supply hose 42 can be heated but is not cooled. Consequently, the temperature of the gas trap 34 is controlled for low outside temperatures. The temperature sensor 106 in the gas trap heat exchanger block 88 provides a temperature feedback. The heat exchanger block 88 in turn heats the humid sample gas recovered from the drilling mud fluid to avoid sample freezing or condensation in the gas trap during winter conditions. The co-located tubes 42, 46 and 50 within sheath 40 provide a heat exchange surface along their length, principally between the main air supply hose 42 and the sample supply tube 50 to provide heating to the sample gas when it leaves the gas trap 34. The heated air supplied to the gas trap 34 exits the heat exchanger block 88 where it is supplied to power and warm the air-motor 44, promoting prolonged motor life expectancy in winter operation.

Heater 122, the activation of which is under the control of controller 120, heats the compressed air supplied to analyzer 26. Controller 120 activates heater 122 based on temperature data supplied on signalling line 52. A set point temperature can be input to controller 120 using suitable input means such as keypad 124. When the gas trap falls below a set point temperature, for example, 32° C., heater 122 is activated to heat the compressed air supplied to the gas trap, the main flow of which will be the air supplied to operate pneumatic motor 44 via coupling 42'. Conversely, when the temperature of the gas trap exceeds a set point temperature, for example 34° C., controller 120 turns off heater 122 to cease the supply of further heat to the gas trap.

The main air supply hose 42 that carries air from the analyser 26 carries the air supplied at a controlled variable pressure and temperature. As noted, the compressed air is heated when the ambient temperature of the gas trap falls below a specified set point.

The analyser 26 operates to control the operation of gas trap 34. The bubbler air supply tube 46 couples to fitting 46' and the primary motor air supply tube 42 couples to coupling 42'. The gas sample recovered from the gas trap is supplied to the analyzer 26 via sample tube 50, which couples to sample tube coupling 50'. A pressure control valve 126 controls the pressure of the flow of air therethrough under the control of controller 120. The speed of rotation of the gas trap motor 44 is provided to controller 120, via the trap signalling line 52.

In operation, the gas trap 34 may become fouled by mud clogging the sample tube gas sample extraction port 84 or by water forming in the gas sample tube 50. These conditions will interfere with the operation of the analysis system, for example, cause a reduction in the sample gas flow rate. To effect self cleaning, gas sample variable control valve 136 is closed and a reverse flow of compressed air to the gas sample supply tube 50 is effected by opening reversing valve 138 to supply compressed air to the sample supply tube 50 via coupling 50'. In this manner, analyzer 26 operates to effect a cleaning process of the gas trap.

The gas trap cleaning process may be carried out periodically during the operation of the gas trap. For example, controller 120 can initiate the self cleaning process periodically every few hours, such as every 4 hours. For further refinement of the self cleaning process, the controller 120 can monitor the sample gas flow rate and initiate a self cleaning process when the sample gas flow rate falls below a predetermined threshold. To initiate self cleaning based on sample gas flow rates, controller 120 monitors the sample gas flow rate by using the sample flow sensor 132. When a reduction in sample gas flow rates below the threshold amount occurs, controller 120 reconfigures the apparatus to effect a self-cleaning process.

Figure 8:
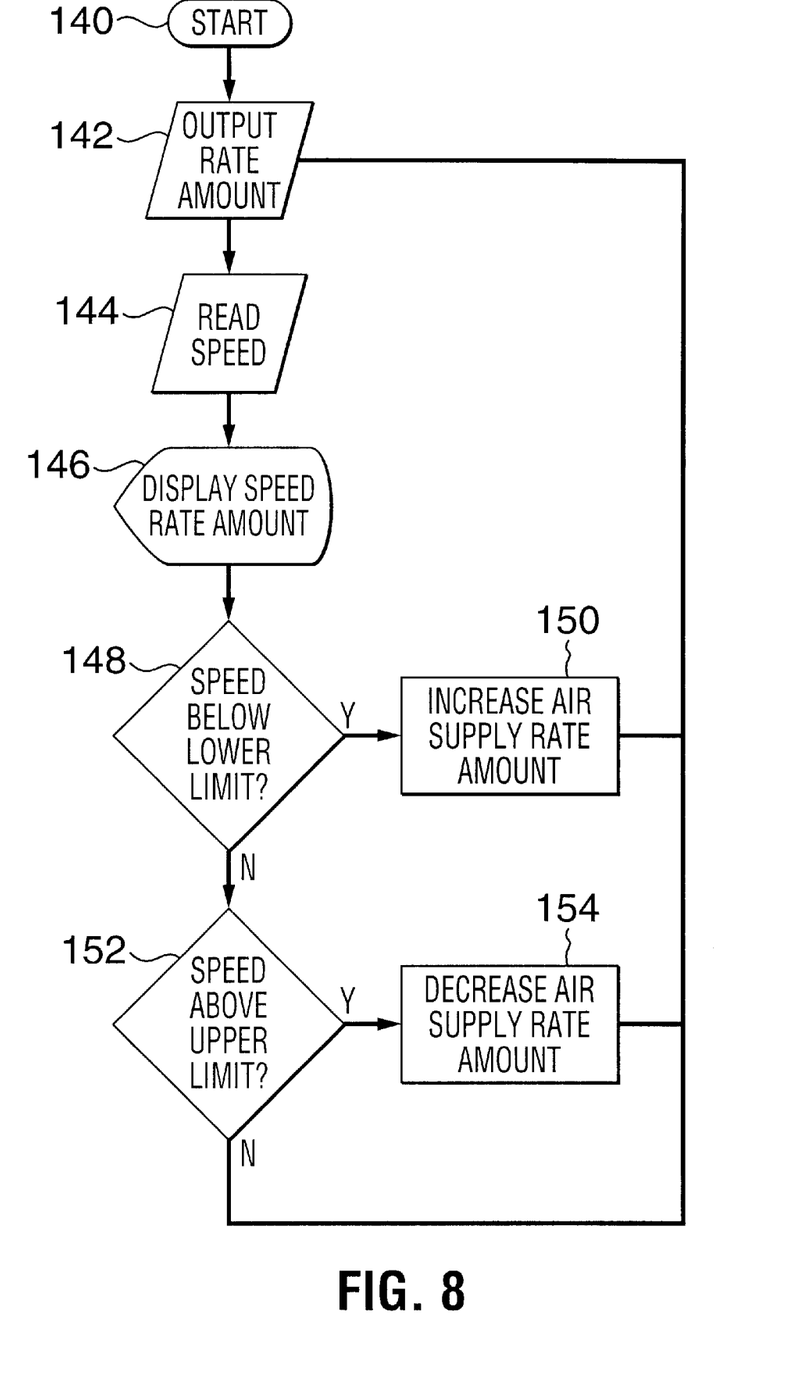
FIG. 8 is a flow chart representation of a relative viscosity measurement process control loop performed by the controller of FIG. 7.

FIG. 8 shows a flow chart representation of a relative fluid viscosity measurement process loop carried out by the gas trap controller 120. The process loop serves to operate the pressure flow control valve 126 based on rotational feed back received from rotational sensor 102. A the start of the speed control process, indicated by 140, a set point speed, for example 1700 RPM and an initial pressure amount, which will effect an initial compressed air flow rate, is established. The compressed air pressure amount setting value is output to pressure control valve 126 as indicated by process box 142. The actual RPM reading is then obtained from the rotational sensor as indicated by input box 144. The RPM reading and pressure amount to effect the target flow rate can be output to a suitable output device such as a display or logged to a file or sent over a communications link to a remote computer, as indicated by output box 146. The actual RPM speed of the motor is compared to a lower threshold at decision box 148. If the speed is below the lower threshold amount, the "Y" exit of the decision box is taken and the compressed air rate amount setting value is increased as indicated by process box 150. The process loop will continue with the changed compressed air rate amount setting value being output to the pressure control valve 126 as indicated by process box 142. If the result of the comparison of decision box 148 is that the air motor 44 speed is not below the lower threshold amount, then the "N" exit of the decision box is taken and air motor speed is next compared to an upper threshold limit as indicated by decision box 152. If the result of the comparison at decision box 152 is that the air motor 44 speed is above the upper threshold amount, the "Y" exit of the decision box is taken and the compressed air pressure rate amount setting value is decreased as indicated by process box 154. The process loop will continue with the changed compressed air pressure rate amount setting value being output to the pressure control valve 126 as indicated by process box 142.

Thus, when the rotational speed of the motor 44 decreases, controller 120 operates to open valve 126 to increase the pressure and consequently the flow of compressed air to the gas trap motor. Opening valve 126 effects an increase in the pressure and flow of compressed air, and therefore the power, supplied to the motor 44 to assist in maintaining a constant motor RPM. Similarly, when the rotational speed of motor 44 increases, controller 120 operates to close the variable control valve 126 to reduce the flow of compressed air therethrough. Consequently, the flow of compressed air or the amount of power supplied to the gas trap motor 44 will decrease to assist in maintaining a constant motor RPM. In this manner, the rate of supply of compressed air is varied to control the RPM of the air motor 44 to maintain a pre-set speed, for example, 1700 RPM. The rotational speed of air motor 44 is fed back to the controller 120 from the rotational sensor 102.

This allows for constant speed agitation of the mud in the sample canister of the gas trap and results in gas readings that are consistent even with variable mud viscosity. Controller initiated variation in the rate of compressed air supply to maintain constant speed of the air motor 44 provides a relative indication of mud viscosity and can be monitored by controller and output on an output means such as display 125. Display 125 is preferably remote from analyser 26, as for example, at a remote computer system.

Restrictor 130 sets the constant rate of supply of the bubbler air supplied to the gas trap 26. The sample received from the gas trap arrives at the analyzer 26 at coupling 50' which couples to the gas sample supply tube 50. The flow rate of the gas sample is monitored by flow meter 132. The sample is drawn into analyzer 26 by means of a pump 134 and the rate of flow of the gas sample into the analyzer 26 is controlled by the sample variable flow control valve 136 to a constant rate, for example, 500 ml. per minute. Restrictor 128 sets the bubbler air supply rate flow to the gas trap 34 and the bubbler air supply rate is greater than the sample gas supply rate. In this manner, analyzer 26 sets the bubbler gas supply rate corresponding to the gas sample supply rate to ensure that excess bubbler air is supplied to the gas trap 34 over the sample gas flow rate which is supplied to the analyser. The excess bubbler air is provided to ensure that the bubbler enclosure 48 is bubbling excess air when the gas trap is in operation. In this way, flooding of the trap is prevented irrespective of an increase in the mud level that the trap is positioned in.

Further, to prevent flooding the gas trap, the gas trap motor speed signalling arriving on gas trap signalling line 52 can be used as a fail safe. When the supply air pressure is too low or not present, the gas trap motor 44 will not be able to maintain the target speed. Controller 120 deactivates sample pump 34 to prevent the analyzer from continuing to operate when the main air pressure supply is too low or not present.

Now that the invention has been explained, numerous substitutions and mechanical equivalents will occur to those skilled in the art without departing from the spirit and scope of the invention, which is defined in the claims appended hereto.

I claim:
1. An apparatus to recover gases from a fluid comprising:
   (i) a sample canister adapted for submersion in a fluid, the sample canister forming sample cavity therein and means to provide a path for the flow of fluid through the sample cavity of the canister via a fluid ingress port and a fluid egress port;
   (ii) means forming a sample extraction port exterior to said sample canister in communication with said sample cavity;
   (iii) a bubbler enclosure attached to said sample canister, the bubbler enclosure having an exit port at a predetermined location in relation to said sample container and a supply port adapted to receive a supply of pressurized gas; and
   (iv) means forming a passage extending between said sample canister and said bubbler enclosure to provide a path for communication of pressurized gas from said supply port to the sample cavity of the sample canister; whereby when the sample canister is submersed in a fluid, a supply of pressurized gas to the inlet port of said bubbler enclosure will result in a level of fluid within said sample cavity of the sample canister correspondingly set by the exit port location of the bubbler enclosure.

2. The apparatus of claim 1 further including agitator means rotatably disposed in the sample cavity of said sample canister.

3. The apparatus of claim 2 further including motor means to drive said agitator.

4. The apparatus of claim 3 wherein said motor means comprises a pneumatic motor.

5. The apparatus of claim 4 further including a source of pressurized air.

6. The apparatus of claim 5 further including apparatus to operate in freezing conditions comprising:
   (i) heater means to heat pressurized air from said source of pressurized air; and
   (ii) a heat exchanger block disposed on said means forming a passage extending between said sample canister and said bubbler enclosure to recover heat from said pressurized air.

7. The apparatus of claim 6 wherein said heat exchanger block is a maze flow heat exchanger.

8. The apparatus of claim 1 further including further including apparatus to operate in freezing conditions comprising a gas heat exchanger to recover heat from pressurized air to heat a gas sample.

9. The apparatus of claim 8 wherein said gas heat exchanger comprises:
   (i) a sample tube for transport of a gas sample;
   (ii) a heated air supply tube; and
   (iii) coupling means to couple said sample tube to said heated air supply tube to facilitate heat exchange therebetween.

10. The apparatus of claim 9 wherein said coupling means comprises an insulating sheath surrounding said sample tube and said compressed air supply tube.

11. An apparatus to recover gases from a fluid comprising:
    (i) a sample container adapted for submersion in a fluid, the sample container forming sample cavity therein and means to provide a path for the flow of fluid through the sample cavity of the container via a fluid ingress port and a fluid egress port;
    (ii) means forming a sample extraction port exterior to said sample container in communication with said sample cavity;
    (iii) agitator means rotatably disposed within the sample cavity of said sample canister;
    (iv) motor means to drive said agitator;
    (v) a bubbler enclosure attached to said sample container, the bubbler enclosure having an exit port at a predetermined location in relation to said sample container and a supply port adapted to receive a supply of pressurized gas; and
    (vi) means forming a passage extending between said sample container and said bubbler enclosure to provide a path for communication of pressurized gas from said supply port to the sample cavity of the sample container.

12. The apparatus of claim 11 further including a source of pressurized air.

13. The apparatus of claim 12 further including:
    (i) heater means to heat pressurized air from said source of pressurized air; and
    (ii) a heat exchanger block disposed on said means forming a passage extending between said sample canister and said bubbler enclosure to recover heat from said pressurized air.

14. The apparatus of claim 11 wherein said heat exchanger block is a maze flow heat exchanger.

15. The apparatus of claim 11 further including a sample heat exchanger to recover heat from said pressurized air for supply to a gas sample.

16. The apparatus of claim 15 wherein said sample heat exchanger comprises:
    (i) a sample tube for transport of a sample gas;
    (ii) a heated air supply tube; and
    (iii) coupling means to couple said sample tube to said heated air supply tube to facilitate heat exchange therebetween.

17. The apparatus of claim 16 wherein said coupling means comprises an insulating sheath surrounding said sample tube and said compressed air supply tube.

18. An apparatus to recover gases from a fluid operable in freezing conditions comprising:
    (i) a sample container adapted for submersion in a fluid, the sample container forming sample cavity therein and means to provide a path for the flow of fluid through the sample cavity of the container via a fluid ingress port and a fluid egress port;
    (ii) means forming a sample extraction port exterior to said sample container in communication with said sample cavity;
    (iii) agitator means rotatably disposed within the sample cavity of said sample canister;
    (iv) motor means to drive said agitator;
    (v) a bubbler enclosure attached to said sample container, the bubbler enclosure having an exit port at a predetermined location in relation to said sample container and a supply port adapted to receive a supply of pressurized gas;
    (vi) means forming a passage extending between said sample container and said bubbler enclosure to provide a path for communication of pressurized gas from said supply port to the sample cavity of the sample container;
    (vii) a source of pressurized air;
    (viii) heater means to heat pressurized air from said source of pressurized air; and
    (ix) a heat exchanger block disposed on said means forming a passage extending between said sample canister and said bubbler enclosure to recover heat from said pressurized air.

* * * * *